United States Patent [19]

Cormack

[11] Patent Number: 4,900,916
[45] Date of Patent: Feb. 13, 1990

[54] SYSTEM EMPLOYING PRECONDITIONED RADIATION FOR DETECTING DEFECTS IN TRANSPARENT OBJECTS

[75] Inventor: Robert H. Cormack, Boulder, Colo.
[73] Assignee: Ball Corporation, Muncie, Ind.
[21] Appl. No.: 163,277
[22] Filed: Mar. 2, 1988
[51] Int. Cl.[4] .............................. G01N 9/04
[52] U.S. Cl. ................... 250/223 B; 356/240
[58] Field of Search ............... 250/223 B; 356/240, 356/239; 209/526

[56] References Cited

U.S. PATENT DOCUMENTS

| | | | |
|---|---|---|---|
| 4,201,338 | 5/1980 | Keller | 250/223 B |
| 4,230,266 | 10/1980 | Juvinall | 250/223 B |
| 4,547,067 | 10/1985 | Watanabe | |
| 4,606,634 | 8/1986 | Bieringer | 250/223 B |
| 4,610,542 | 9/1986 | Ringlien | |
| 4,682,023 | 7/1987 | Yoshida | |

OTHER PUBLICATIONS

R. Cormack et al., "Optical and Digital Pattern Recognition", Proceedings of the SPIE-The International Society for Optical Engineering, vol. 754, Jan. 13-15, 1987, Los Angeles, Calif.

Primary Examiner—David C. Nelms
Assistant Examiner—Khaled Sharmi
Attorney, Agent, or Firm—Sheridan, Ross & McIntosh

[57] ABSTRACT

An apparatus and method for inspecting transparent objects is disclosed. The apparatus employs preconditioned radiation to detect defects having small radii of curvature or other such highly refractive surfaces and discriminate them from desirable markings having larger radii of curvature. The apparatus comprises a radiation source, means for selecting angular spectrum ranges, means for modifying average angles of incidence, radiation detection means and processing means.

25 Claims, 4 Drawing Sheets

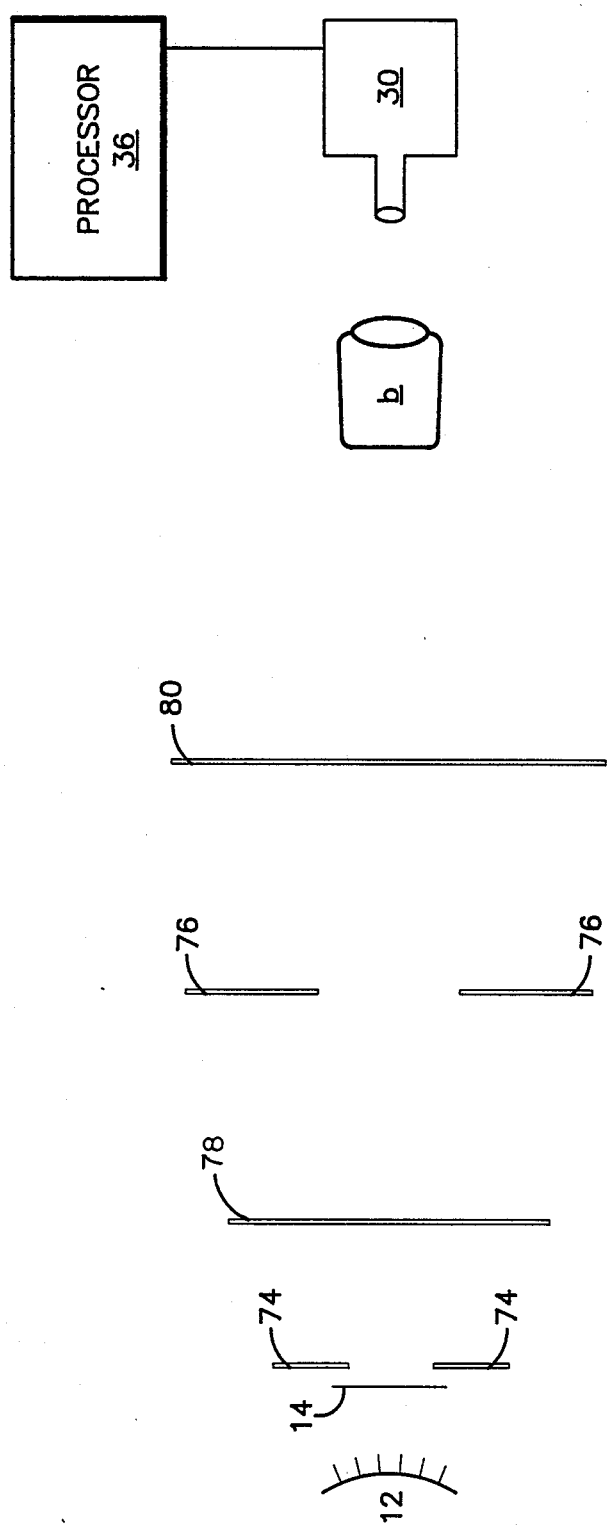

SYSTEM EMPLOYING PRECONDITIONED RADIATION FOR DETECTING DEFECTS IN TRANSPARENT OBJECTS

FIELD OF THE INVENTION

This invention relates to lighting systems used for inspecting transparent objects, and more particularly, a system wherein preconditioned radiation is employed to detect defects having relatively small radii of curvature.

BACKGROUND OF THE INVENTION

Lighting systems for inspecting glassware are well known in the art. For example, U.S. Pat. No. 4,682,023 by Yoshida, issued July 21, 1987, describes a system for detecting defects in the mouths of bottles. In one embodiment, this system comprises a light source followed by a diffuser and a mask placed below the bottle to be inspected and an additional mask and a photoelectric sensor placed above the bottle. The light enters the bottle from its bottom, passes through the inside of the sidewall of the bottle, travels upward within the sidewall and is then emitted from the mouth to be detected by the photoelectric sensor. An electric processor determines whether there are areas in which the light has been blocked, which is indicative of a defect.

One disadvantage of the system disclosed in the Yoshida patent is that it is only capable of detecting defects which inhibit the transmission of light upward through the sidewall of a bottle. Therefore, defects located outside of, but adjacent to the sidewall of a bottle often cannot be detected using this system. Another disadvantage is that if it is desired to inspect both the mouth and the bottom of the bottle, then a beam splitter, two separate masks and two separate photoelectric sensors must be employed, as illustrated in FIG. 7 of the Yoshida patent.

A system which is capable of detecting both opaque and transparent defects in bottles is disclosed in U.S. Pat. No. 4,547,067 by Watanabe, issued Oct. 15, 1985. Watanabe discloses a system that can be employed to inspect either the sidewall of a bottle or the bottom of a bottle. However, there is no disclosure of inspecting both areas simultaneously. Another disadvantage with the system disclosed in the Watanabe patent is that it is relatively complex The system requires the use of a polarizer and a quarter wave plate placed between the light source and the bottle and an additional polarizer and quarter wave plate placed between the bottle and the radiation detection means.

Yet another system is disclosed in U.S. Pat. No. 4,610,542 by Ringlien, issued Sept. 9, 1986. This patent employs generally horizontal collimated light having a vertical gradient of brightness produced by placing a showcase light behind the upper area of a diffuser plate. The light passes through a first lens, a bottle to be inspected, a second lens, and finally illuminates a radiation detection means comprising a vertical array of pixels. Refractive defects change the intensity of the radiation that strikes the pixels and, therefore, this system can detect transparent refractive defects in the sidewalls of bottles. There is no disclosure, however, of detecting defects in the bottoms of bottles.

One defect commonly encountered in glassware is what is referred to as "stuck glass". During the manufacture of glassware, such as bottles, a newly formed, hot bottle will occasionally shatter. Some of the resulting pieces of glass will land inside adjacent bottles, entering through the mouth and sticking to the bottoms or the lower portion of the sidewalls of the bottles. Because the mouths of most bottles are typically relatively small, the vast majority of the stuck glass found inside bottles will be on the bottom or the lower half of the sidewalls of the bottle. Stuck glass on the inside of bottles can be dangerous because, if food or beverage products are placed in the bottle, the stuck glass may eventually break off and be consumed, causing injury to the consumer.

Therefore, it would be advantageous to provide an inspection system which can detect transparent defects, such as stuck glass, in transparent objects, such as bottles and jars. It would also be advantageous to provide an inspection system that can simultaneously inspect the bottom and the lower sidewall portions of jars and bottles. Furthermore, it would be advantageous to provide an inspection system which can discriminate between undesirable defects, such as stuck glass, which possess sharp edges having small radii of curvature, from desirable markings, such as a mold marking, which have larger radii of curvature.

SUMMARY OF THE INVENTION

The present invention provides an apparatus and method for inspecting transparent objects having complex shapes. In accordance with the invention, an object is inspected using "preconditioned radiation" in order to detect defects with relatively small radii of curvature or other such highly refractive surfaces, and discriminate such defects from desirable markings and acceptable defects with larger radii of curvature.

The object to be inspected is illuminated with the "preconditioned radiation", and a radiation detection means is provided so that, in a preferred embodiment, at least a portion of that radiation striking an undesirable defect which would, but for the defect, encounter the radiation detection means, does not encounter the radiation detection means due to the refracting, or blocking, effect of the defect. The radiation detection means generates signals which correspond to the intensity of the radiation which strikes it. The signals are analyzed by processing means in order to determine whether there are undesirable defects. The present system has been advantageously employed to detect defects having dimensions as small as 0.004 inch.

As used herein, "preconditioned radiation" is radiation that is conditioned in such a way that the "angular spectrum ranges" and "average angles of incidence" at all points of interest on or within a bottle to be inspected are appropriate for detecting defects at such points, in view of the positioning of the radiation detection means and "angles of acceptance" for radiation incident upon the radiation detection means.

For present purposes, the term "angular spectrum ranges" shall mean the ranges of ray directions of radiation incident upon points of interest on an object. By way of example, if radiation is provided to an object by shining a diffuse light source through a stop(s) with a central aperture(s), and next through a lens positioned greater than one focal length from the stop(s), then the angular spectrum ranges for points on the object will primarily be a function of the size of the aperture(s) and the relative position of the lens and the object. If the aperture(s) of the stop(s) is opened to a greater diameter, and the axial geometry of the system elements remains constant, the angular spectrum ranges for points on the object will increase If the aperture(s) of the stop(s) is closed to a smaller diameter, the angular spectrum ranges will decrease. In FIG. 1, angular spectrum ranges 4, 5 and 6 are illustrated for three different points on bottle b. Preferably the angular spectrum ranges for detection of defects in the present invention should be less than about 60°.

For present purposes, the terms "average incidence angle" and "average angle of incidence" shall mean the average angle at which the radiation strikes a point on the object to be inspected. For instance, if the object has a flat bottom which is perpendicular to the light source, then the average incidence angle on the center of the bottom will be 90°, as illustrated by angle 7 in FIG. 1. The average incidence angle will vary, depending the shape of the object as illustrated by angles 8 and 9 at the sidewall portion of bottle b in FIG. 1. In the present invention, the average incidence angles for points on the object are principally varied by means of a "incidence angle modifier". In preferred embodiments, this incidence angle modifier is a Fresnel lens.

For present purposes, the terms "acceptance angles" and "angles of acceptance" shall mean the angular ranges within which light, which has passed through points of interest on an object to be inspected, must fall in order to be detected by the radiation detection means. In FIG. 2, acceptance angles 45, 46 and 47 are illustrated for three different points on the transparent object.

The apparatus of the present invention comprises a radiation source followed by means for selecting angular spectrum ranges for points of interest on the object to be inspected, means for modifying the average incidence angles of radiation incident upon such points, means for detecting the radiation illuminating the object to be inspected, and means for analyzing the data provided by the radiation detection means. Preferably, the radiation source comprises a white light source; the means for selecting the angular spectrum ranges for points on the object comprises a diffuser followed by a stop; the means for modifying the average angles of incidence comprises a lens, such as a Fresnel lens; the radiation detection means comprises a lens and a photodiode array which transmits signals corresponding to the intensity of radiation incident upon each diode within the array; and the analyzing means comprises an electronic processor.

The present invention also provides a method for inspecting a substantially transparent object having a complex shape for undesirable defects having relatively small radii of curvature or other such highly refractive surfaces, and discriminating said defects from desirable markings and acceptable defects having larger radii of curvature. The method comprises illuminating the points of interest on the transparent object with radiation within certain angular spectrum ranges. The angular spectrum ranges are selected in order that at least a portion of the radiation which strikes the defects is refracted, in a preferred embodiment, outside of the acceptance angle of a radiation detection means, while a relatively greater amount of the radiation which strikes non-defect areas remains on paths within the acceptance angle of the radiation detection means. The radiation, prior to striking the transparent object to be inspected, is conditioned so that the average angles of incidence of the radiation incident on the region of interest on a transparent object are such that non-defect areas in the complex-shaped object, in a preferred embodiment, appear more illuminated to the radiation detection means than defects, irrespective of the orientation of the various surfaces of the complex-shaped object relative to the radiation source. The radiation detection means produces signals corresponding to the intensity of the incident radiation and the signals are analyzed in order to determine whether there are defects present on the inspected object.

BRIEF DESCRIPTION OF THE DRAWINGS

FIG. 4 illustrates another embodiment of an apparatus in accordance with the present invention

DETAILED DESCRIPTION OF THE INVENTION

Figure 1:
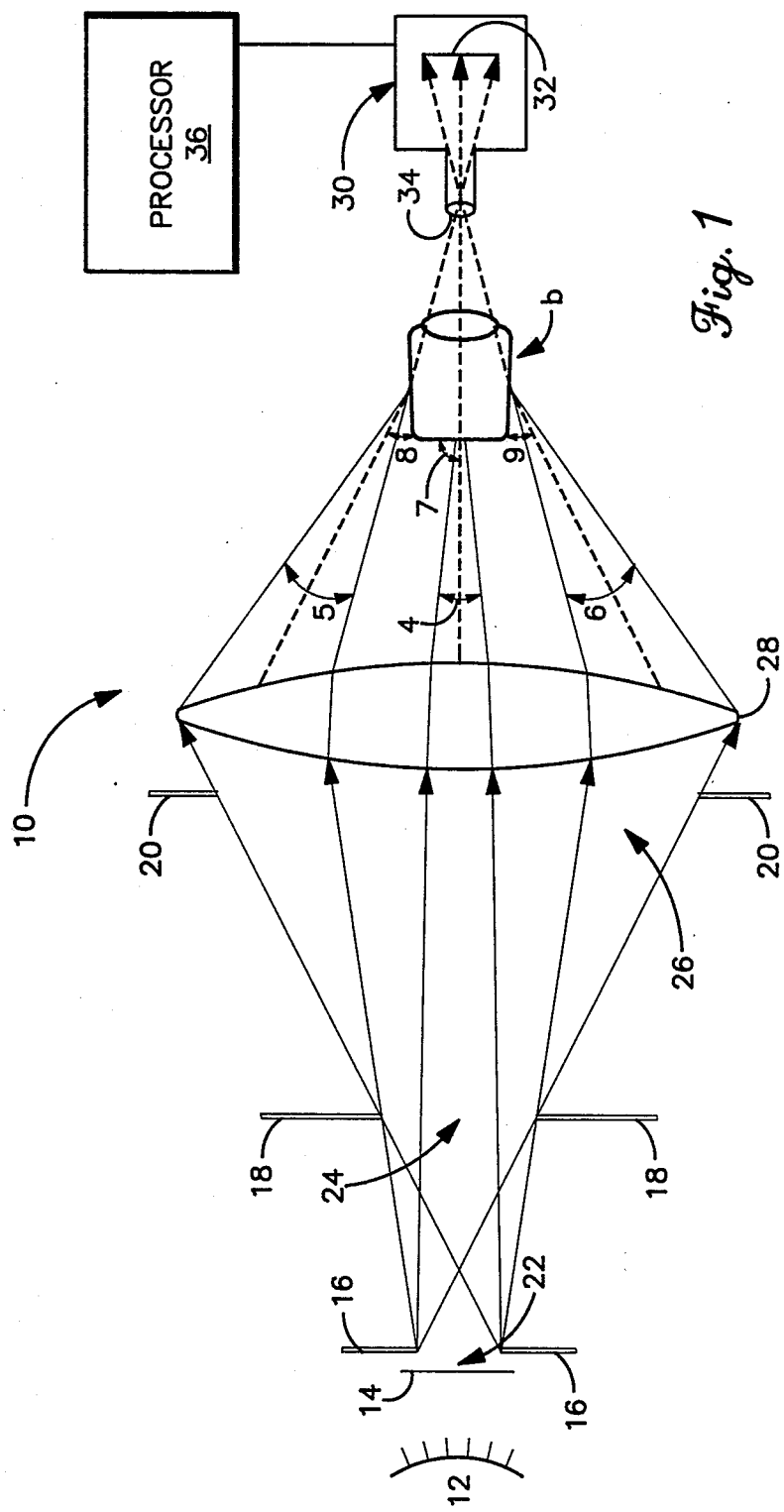
FIG. 1 illustrates one embodiment of an apparatus in accordance with the present invention.

The method and apparatus of the present invention will be explained with reference to the preferred embodiment illustrated in FIG. 1. The apparatus 10 comprises a radiation source which, in FIG. 1, is shown as a white light source 12. Next, there are means for selecting the angular spectrum ranges for radiation incident upon points of interest on the object to be inspected. This is shown as a combination of a diffuser 14 and a plurality of stops 16, 18 and 20 each having a particular diameter aperture 22, 24 and 26. The angular spectrum ranges for radiation beams striking three points on bottle b are shown by angles 4, 5 and 6. The outer limits of the angular spectrum ranges 4, 5 and 6 are determined by the radiation beams at the outer limits of the stops 16, 18 and 20.

After the radiation passes through the means for selecting the angular spectrum ranges, the radiation passes through means for modifying the average angles of incidence for radiation incident upon points of interest on the object to be inspected. This is shown as a lens 28. The average angles of incidence for three points on bottle b are shown by angles 7, 8 and 9.

As will be appreciated by those skilled in the art, the angular spectrum ranges are not determined solely by the position of the diffuser and the size of the stops. The relative positions of the other elements of the inspection system as well as the focal length of the lens will also influence the angular spectrum ranges Additionally, the average incidence angles are not determined solely by the lens 28 but will also be influenced by the relative positions of the other elements of the system.

A substantial portion of the radiation passing through the lens 28 passes through the object to be inspected, as illustrated by bottle b in FIG. 1. Finally, a portion of the radiation strikes a radiation detection means, which in this specific embodiment is a video camera 30 comprising a photo-diode array or charge coupled device 32 and a lens 34. A processor 36 analyzes the output of the radiation detection means 30.

Figure 2:
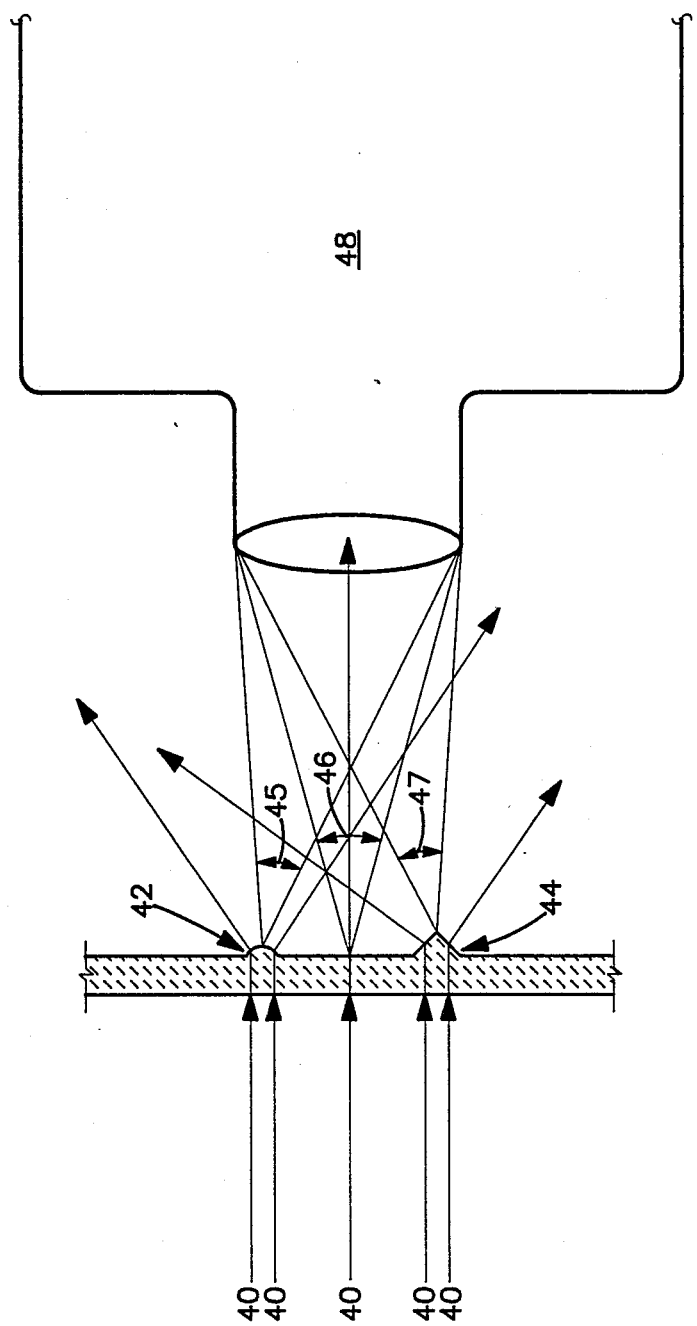
FIG. 2 illustrates collimated radiation beams striking a marking having a relatively large radius of curvature and striking a defect having a relatively small radius of curvature.

The means for selecting the angular spectrum ranges can be any means known in the art. For instance, a diffuser followed by at least one stop with a central aperature. Alternatively, if extremely small angular spectrum ranges are desired, a diffuser placed at a relatively large distance from the transparent object to be inspected can be used. This results in radiation which is substantially collimated. In other words, the beams are substantially parallel. In such instances, defects having relatively large radii of curvature may be detected. This is illustrated in FIG. 2, which shows collimated beams of radiation 40 striking a defect having a large radius of curvature 42 and a defect having a smaller radius of curvature 44. In both instances, a portion of the collimated radiation incident upon the defects is refracted outside of the acceptance angles 45 and 47 of the radiation detection means 48. However, analogous radiation which passes through a non-defect area is within the acceptance angle 46 of the radiation detection means 48. A system using collimated light will have difficulty discriminating between acceptable and unacceptable defects having large or small radii of curvature respectively, since both types of defects will tend to be imaged as relatively dark areas at the radiation detection means 48.

Figure 3:
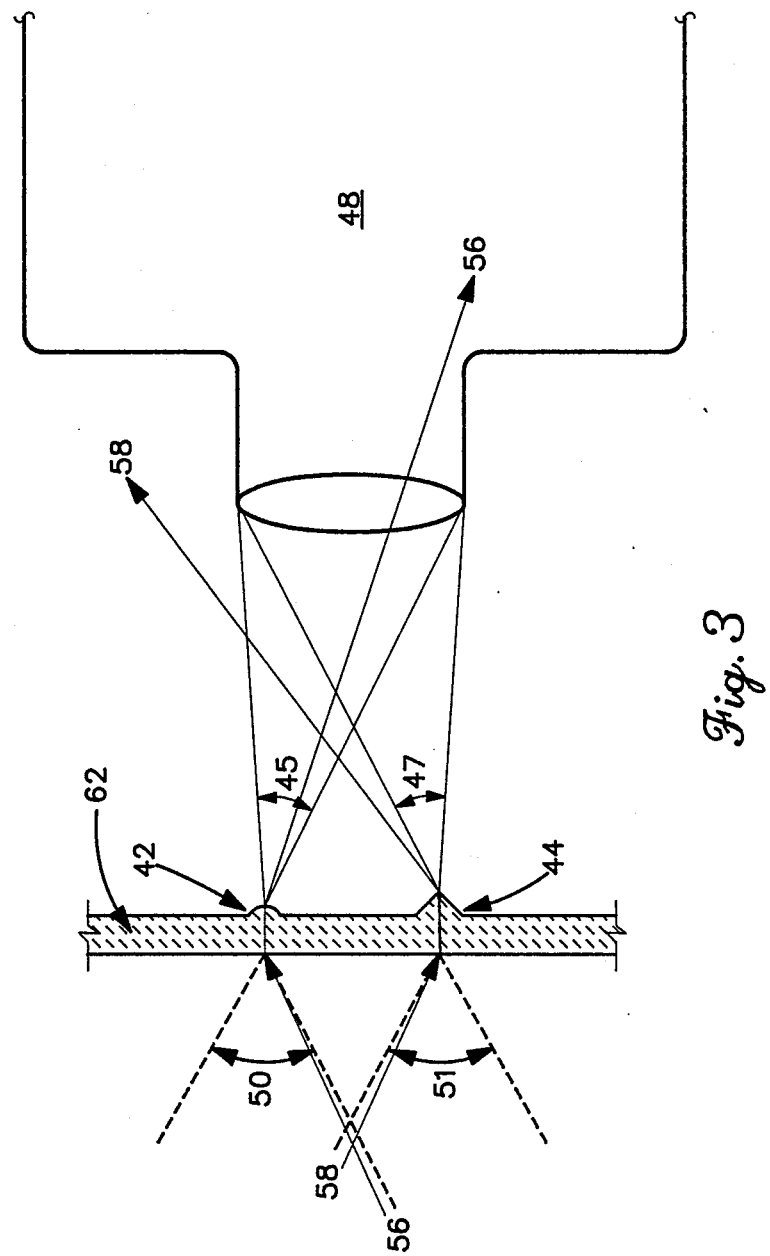
FIG. 3 illustrates radiation striking a marking having a relatively large radius of curvature and also striking a defect having a smaller radius of curvature, wherein the angular spectrum ranges for the radiation at such points is substantially limited.

As the angular spectrum ranges are increased, the radii of curvature of defects which can be detected will decrease. FIG. 3 illustrates how radiation having angular spectrum ranges 50 and 51 at two different points on an object is effected differently by a desirable marking having a large radius of curvature 42 and a defect having a small radius of curvature 44. The radiation within the limited angular spectrum range 50 strikes the marking 42 and some of the radiation 56 is fracted and falls within the acceptance angle 45 of the radiation detection means 48. In contrast, the radiation within the angular spectrum range 51 strikes the defect 44 and some of the radiation 58, analogous with the radiation 56, is refracted outside of the acceptance angle 47 of the radiation detection means 48. As a result, it should be appreciated that the intensity of all radiation that has passed through defect 44 and is detected by the radiation detection means 48 is less than the intensity of detected radiation that has passed through adjacent non-defect areas.

An alternative embodiment employs a diffuser followed by an opaque central stop In this way, the angular spectrum ranges comprise radiation which strikes the object to be inspected at angles greater than some minimum limit. Radiation passing through the non-defect areas at angles larger than some certain minimum angle will remain substantially outside of the acceptance angle of the radiation detection means. Radiation which strikes a defect is refracted to a greater extent, and therefore a greater portion falls within the acceptance angle of the radiation detection means and will register as having a certain light intensity. This results in an image at the radiation detection means comprising relatively dark areas corresponding to the non-defect areas and lighter areas corresponding to the defects.

The means for modifying the average angles of incidence can be any means known in the art. This means allows the incidence angles to be varied in accordance with the complex shape of the objects to be inspected. This would not be necessary if, for instance, the transparent object to be inspected consisted merely of a flat pane of glass. However, since objects such as bottles have a bottom portion, heel portion and sidewall portion, the average angles of incidence must be varied in accordance with the orientation of the areas to be inspected relative to the radiation source and radiation detection means. This modification can be accomplished by a lens such as a Fresnel lens. The average angles of incidence are affected by the focal length of the lens, as well as the location of the lens relative to the other elements of the inspection system.

The amount of incidence angle modification required will be a function of the shape of the object and the refractive index of the object. Surprisingly, it has been found that lenses, and in particular Fresnel lenses, which provide for relatively high spherical aberration provide better results with bottle-shaped objects than lenses which provide for relatively less spherical aberration. When a lens with spherical aberration is employed, it is advantageous to use multiple stops to limit the angular spectrum ranges in a more effective manner.

The transparent object to be inspected is placed between the means for modifying the angles of incidence and the radiation detection means. The present invention offers three advantages. First, using the present invention, it is possible to detect transparent defects within transparent objects. Obviously, opaque defects may also be detected. Second, it is possible to discriminate between undesirable defects which have small radii of curvature or other highly refractive surfaces and desirable markings (e.g., mold markings, identification marks and knurling) which have relatively larger radii of curvature. In order to discriminate between the undesirable defects and the desirable markings, it is necessary to select appropriate angular spectrum ranges. The controlling relationship is that as the radii of curvature of the defects that are to be detected increases or the amount the defects refract radiation decreases, the angular spectrum ranges must be decreased. Third, it is possible to inspect complex shapes, i.e., the bottom and sides of bottles, by modifying the average angles of incidence as the orientation of the area to be inspected changes relative to the light source. The goal is to illuminate the areas that are to be inspected, as viewed from the radiation detection means.

The radiation detection means can be selected from the large variety available to practitioners skilled in the art. The radiation detection means detects radiation which passes through the transparent object being inspected and produces signals corresponding to the intensity of the incident radiation. Most importantly, the radiation detection means must have limited acceptance angles for points of interest on the object to be inspected. The acceptance angles of the radiation detection means and the angular spectrum ranges of the preconditioned radiation for such points primarily determine which defects will have a high degree of contrast relative to adjacent non-defect areas, and which markings will have relatively low contrast with the adjacent areas. The average incidence angles primarily determine which areas of the object will be capable of being inspected.

As illustrated in FIG. 3, as the radiation within the selected angular spectrum ranges 50 and 51 strikes areas 42 and 44 on the transparent object 62, the radiation is refracted towards the radiation detection means 48. If a relatively high portion of the radiation which strikes area 44 is refracted outside of acceptance angle 47 of the radiation detection means 48, then area 44 will be determined to correspond to a defect area. Alternatively, if a relatively high portion of the radiation striking area 42 falls within acceptance angle 45 of the radiation detection means 48, then area 42 will be classified as a non-defect area.

It should be understood that the above explanation applies when a stop with a central aperature is used. If an opaque central stop is used, the opposite would be true. In other words, the defect areas would refract relatively more light within the acceptance angle and therefore the defect would show up as a light area. The non-defect areas would refract relatively less light within the acceptance angle and therefore the non-defect areas would appear darker.

The signals produced by the radiation detection means 32 are analyzed by a processing means 36. As noted above, the signals relate to the intensity of the radiation incident upon the radiation detection means 32. The purpose of the processing means is to determine whether the intensity signals indicate the presence of defect areas on the object. In a preferred embodiment, for example, a photo-diode array will generate separate signals corresponding with the intensity of radiation incident upon each diode within the array. As can be appreciated, the intensity signals also correspond with the amount of radiation passing through particular regions of interest on the inspected object and received by the radiation detection means. The signals are analyzed by the processing means 36 in a known manner to determine the intensity gradient of radiation incident upon adjacent diodes. When a gradient associated with a particular region of interest on an object is greater than an acceptable, predetermined value, the presence of a defect within such region of the inspected object is indicated. As a result, the processor can electronically instruct interconnected devices to reject the inspected object from the associated system in which the present invention is employed.

The various parameters for the system of the present invention depend upon the size and shape of the object to be inspected, its refractive index, and the radii of curvature of or amount of refraction produced by the defects to be detected. For example, if the transparent object is larger, a larger lens could be used.

When setting the parameters, a desirable starting point is to image the diffuser in the center of the lens of the radiation detection means. This will result in a uniformly illuminated field of view because the diffuser will be maximally out of focus. Next, the object is placed between the radiation source and the radiation detection means, and its position is adjusted until the portions of the object to be inspected are illuminated. Alternatively, the lens and light source may be adjusted in order to obtain the desired illumination.

A helpful way to visualize the system is to imagine the illumination from the point of view of the radiation detection means. The average incidence angles are chosen so that the radiation detection means will see an illuminated background when looking through the transparent object when markings on such object have a radius of curvature less than some threshold amount, but will see outside the illumination source when looking at a defect with a radius of curvature that is smaller than the threshold amount or when looking through a relatively highly refractive surface. Thus, small pieces of stuck glass produce dark images against a light background when a stop with a central aperature is employed. When an opaque central stop is employed, one will observe a dark background when looking through the transparent object, and a defect will produce a light area.

In general, the diffuser is placed so that it is imaged at the position of a radiation detection means lens. This allows light from every point on the diffuser to contribute to every point in the field of view. Out of the many configurations of the lens/diffuser/radiation detection means that preserve the relationship, one is chosen to maximize the desired result of suppressing the normal bottle features and enhancing the image of highly refractive defects. The principle is to match the convergence of the illumination and the object position so that radiation refracted by desired curved surfaces of the bottle still reaches the radiation detection means. For some bottles with sharply curved heels, this can best be accomplished by moving the diffuser image slightly away from the radiation detection means lens towards the bottle. The size of the circular stop over the diffuser is then adjusted to obtain the desired angular spectrum ranges for points of interest on the bottle and hence the degree of refraction required to create a relatively dark area in the image.

The area of illumination is directly influenced by the size of the lens and its distance from the object. The size of the diffuser plate and stops, their distance from the lens, and the focal length of the lens affect the average incidence angle on a given point on the bottle, as well as the angular spectrum range. A compound lens as shown in FIG. 4 can be used to allow for a more compact system or provide more adjustment with additional stops. FIG. 4 illustrates a radiation source 12, a diffuser 14, two stops 4, 76, two lenses 78, 80, the transparent object being inspected b, a radiation detection means 30, and a processor 36.

While various embodiments of the present invention have been described in detail, it is apparent that modifications and adaptations of those embodiments will occur to those skilled in the art. However, it is to be expressly understood that such modifications and adaptations are within the spirit and scope of the present invention, as set forth in the following claims.

What is claimed is:

1. A method for inspecting a substantially transparent object having a complex shape wherein substantially transparent defects having relatively highly refractive surfaces on areas of interest of said object are detected and substantially transparent markings having surfaces which are less refractive on areas of interest of said object are not detected, said method comprising:
   (a) illuminating said transparent object with radiation having certain angular spectrum ranges for points of interest on said object;
   (b) selecting said angular spectrum ranges in order that radiation which is incident upon said transparent object and which passes through said defects is refracted outside of a limited angle of acceptance to a greater extent than is radiation which is incident upon adjacent non-defect areas;
   (c) conditioning said radiation in such a manner that a plurality of rays emanating from a single point on a source of said radiation are non-parallel prior to their incidence on said transparent object in order to provide radiation having average angles of incidence at various points of interest on said complex-shaped transparent object, said average angles of incidence being provided such that non-defect areas of said complex-shaped transparent object which are to be inspected are illuminated when viewed from a position of a means employed to detect the intensity of said radiation;

(d) detecting the intensity of said radiation which falls within said limited angle of acceptance after having passed through said transparent object; and (e) analyzing the intensity of said radiation to determine whether defects are present.

2. The method of claim 1, wherein radiation having certain angular spectrum ranges is primarily obtained by passing radiation from a diffuse radiation source through at least one stop having a central aperture prior to its incidence upon said transparent object.

3. The method of claim 2, wherein said angular spectrum ranges are increased by increasing the size of said aperature or alternatively said angular spectrum ranges are decreased by decreasing the size of said aperature.

4. The method of claim 1, wherein said conditioning of said radiation prior to its incidence upon said transparent object is primarily accomplished by passing said radiation through a lens.

5. The method of claim 4, wherein said lens is a Fresnel lens.

6. The method of claim 5, wherein said Fresnel lens has a certain amount of spherical aberration.

7. A method for inspecting a substantially transparent object having a complex shape wherein substantially transparent defects having highly refractive surfaces on areas of interest of said object are detected and substantially transparent markings having surfaces which are less refractive on areas of interest of said object are not detected, said method comprising:

(a) illuminating said transparent object with radiation having certain angular spectrum ranges for points of interest on said object;

(b) selecting said angular spectrum ranges in order that radiation which is incident upon said transparent object and which passes through said defects is refracted within a limited angle of acceptance to a greater extent than is radiation which is incident upon adjacent non-defect areas;

(c) conditioning said radiation in such a manner that a plurality of rays emanating from a single point on a source of said radiation are non-parallel prior to their incidence on said transparent object in order that defects within areas of said transparent object which are to be inspected are illuminated when viewed from a position of a means employed to detect the intensity of said radiation;

(d) detecting the intensity of said radiation which falls within said limited angle of acceptance after having passed through said transparent object; and (e) analyzing the intensity of said radiation to determine whether defects are present.

8. The method of claim 7, wherein radiation having certain angular spectrum ranges is primarily obtained by passing radiation from a diffuse radiation source around at least one central opaque stop prior to its incidence upon said transparent object.

9. The method of claim 8, wherein said angular spectrum ranges are decreased by increasing the size of said stop or alternatively said angular spectrum ranges are increased by decreasing the size of said stop.

10. An apparatus for inspecting areas of interest on a substantially transparent object having a complex shape wherein said apparatus discriminates between substantially transparent defects having relatively highly refractive surfaces and transparent markings having surfaces which are less refractive, said apparatus comprising:

(a) a radiation detection means which produces signals corresponding to the intensity of incident radiation falling within a limited angle of acceptance;

(b) a source of radiation which illuminates said transparent object with radiation having certain angular spectrum ranges at points of interest on said object;

(c) means for modifying the average angles of incidence of the radiation incident on said transparent object to be inspected wherein a plurality of rays originating from a single point on said source of radiation are non-parallel after passing through said means for modifying the average angles of incidence; and (d) processing means for analyzing the signals produced by said radiation detection means.

11. The apparatus of claim 10, wherein said radiation detection means comprises a charge coupled device.

12. The apparatus of claim 10, wherein said radiation detection means comprises a video camera comprising a charge coupled device and a lens.

13. The apparatus of claim 10, wherein said source of radiation comprises a diffuse light source followed by at least one stop.

14. The apparatus of claim 10, wherein said source of radiation comprises a white light source followed by a diffuser, followed by at least one stop.

15. The apparatus of claim 13, wherein said stop comprises a central aperature and said effects are imaged at said radiation detection means as relatively dark areas against a lighter background.

16. The apparatus of claim 13, wherein said stop comprises an opaque central stop and wherein said defects are imaged at said radiation detection means as relatively light spots against a darker background.

17. The apparatus of claim 10, wherein said means for modifying the average angles of incidence comprises a lens.

18. The apparatus of claim 10, wherein said means for modifying the average angles of incidence comprises a Fresnel lens.

19. The apparatus of claim 10, wherein said means for modifying the average angle of incidence comprises a Fresnel lens having spherical aberration.

20. The apparatus of claim 10, wherein said transparent object is glassware.

21. The apparatus of claim 10, wherein said transparent object is a glass container.

22. The apparatus of claim 10, wherein said transparent object is a bottle or a jar.

23. A method for determining the parameters for an inspection system comprising a radiation detection means comprising a video camera with a limited angle of acceptance, a radiation source comprising a diffuse light source followed by a stop which illuminates a transparent object with radiation having certain angular spectrum ranges at points of interest on the object, means for modifying the average angles of incidence of the radiation incident upon said object at such points, said means comprising a lens, and processing means; wherein said method comprises:

(a) imaging said diffuse light source on a lens of said video camera so as to maximize the light incident at said camera and put the diffuse light source maximally out of focus;

(b) selecting the angular spectrum range so that a greater portion of the light incident on defects in said transparent object is refracted outside of the limited angle of acceptance of the video camera than is the case with light incident upon non-defect areas;

(c) selecting the average angles of incidence so that non-defect areas to be inspected appear illuminated from the point of view of said video camera; and (d) focusing said lens of said video camera on the areas of the transparent object to be inspected.

24. The method of claim 23, wherein said stop is a circular stop and said selection of the angular spectrum ranges is accomplished by selecting a desired diameter for said stop and by adjusting the relative positions of the elements of said inspection system.

25. The method of claim 23, wherein said selection of the average angles of incidence is accomplished by selecting the focal length of said lens and by adjusting the position of said lens relative to the positions of the other elements of said inspection system.

* * * * *

UNITED STATES PATENT AND TRADEMARK OFFICE
CERTIFICATE OF CORRECTION

PATENT NO. : 4,900,916

DATED : February 13, 1990

INVENTOR(S) : Robert H. Cormack

It is certified that error appears in the above-identified patent and that said Letters Patent is hereby corrected as shown below:

Column 1, line 46, insert a period after "complex".

Column 3, line 1, insert a period after "increase".

Column 3, line 15, after "depending" insert --on--.

Column 3, line 16, insert a comma after "object".

Column 4, line 23, insert a period after "invention".

Column 4, line 54, insert a period after "ranges".

Column 5, line 31, delete "fracted" and insert therefor --refracted--.

UNITED STATES PATENT AND TRADEMARK OFFICE
CERTIFICATE OF CORRECTION

PATENT NO. : 4,900,916
DATED      : February 13, 1990
INVENTOR(S) : Robert H. Cormack It is certified that error appears in the above-identified patent and that said Letters Patent is hereby corrected as shown below:

Column 5, line 44, insert a period after "stop".

Column 8, line 29, delete "4" and insert therefor --74--.

Column 10, line 28, delete "effects" and insert therefor --defects--.

Signed and Sealed this

Twelfth Day of February, 1991

Attest:

HARRY F. MANBECK, JR.

*Attesting Officer*  *Commissioner of Patents and Trademarks*